US006387906B1

(12) United States Patent
Meerpoel et al.

(10) Patent No.: US 6,387,906 B1
(45) Date of Patent: May 14, 2002

(54) 2,4,4-TRISUBSTITUTED-1,3-DIOXOLANE ANTIFUNGALS

(76) Inventors: Lieven Meerpoel; Jan Heeres, both of Janssen Pharmaceutica N.V., Turnhoutseweg 30, B-2340 Beerse (BE); Frank Christopher Odds, 210 Kings Gate, Aberdeen AB15 6DQ (GB); Hugo Florent Adolf Vanden Bossche; Louis Jozef Elisabeth Van der Veken, both of Janssen Pharmaceutica N.V., Turnhoutseweg 30, B-2340 Beerse (BE)

( * ) Notice: Subject to any disclaimer, the term of this patent is extended or adjusted under 35 U.S.C. 154(b) by 0 days.

(21) Appl. No.: 09/462,588

(22) PCT Filed: Jul. 7, 1998

(86) PCT No.: PCT/EP98/04194

§ 371 Date: Jan. 7, 2000

§ 102(e) Date: Jan. 7, 2000

(87) PCT Pub. No.: WO99/02523

PCT Pub. Date: Jan. 21, 1999

(30) Foreign Application Priority Data

Jul. 11, 1997 (EP) .............................. 97202181

(51) Int. Cl.[7] ................... C07D 405/14; A61K 31/495; A61P 29/00

(52) U.S. Cl. .............. 514/254.05; 514/254.1; 514/255.03; 514/242; 514/397; 514/398; 514/399; 514/596; 514/597; 514/598; 544/366; 544/374; 544/182

(58) Field of Search ............. 514/254.05, 254.1, 514/255.03, 242, 397, 398, 399, 596, 597, 598; 544/366, 374, 182

(56) References Cited

FOREIGN PATENT DOCUMENTS

| EP | 0 006 711 | 1/1980 |
|---|---|---|
| EP | 0 118 138 | 9/1984 |
| EP | 0 228 125 | 7/1987 |
| EP | 0 402 989 | 12/1990 |
| WO | WO 88/05048 | 7/1988 |
| WO | WO 93/09114 | 5/1995 |
| WO | WO 95/19983 | 7/1995 |

Primary Examiner—Floyd D. Higel
Assistant Examiner—Andrea M. D'Souza
(74) Attorney, Agent, or Firm—Mary A. Appollina

(57) ABSTRACT

The present invention concerns novel compounds of formula (I)

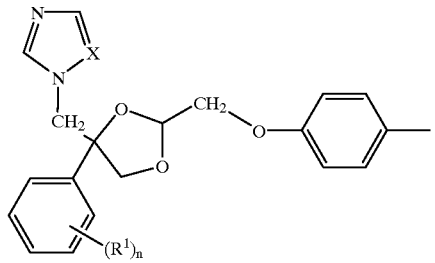

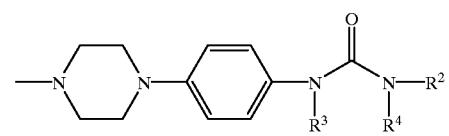

a N-oxide form, a pharmaceutically acceptable acid addition salt or a stereochemically isomeric form thereof, wherein n is zero, 1, 2 or 3; X is N or CH;

each $R^1$ independently is halo, nitro, cyano, amino, hydroxy, $C_{1-4}$alkyl, $C_{1-4}$alkyloxy or trifluoromethyl; $R^2$ is hydrogen; $C_{3-7}$alkenyl; $C_{3-7}$alkynyl, aryl; $C_{3-7}$cycloalkyl; optionally substituted $C_{1-6}$alkyl $R^3$ and $R^4$ each independently are hydrogen, $C_{1-6}$alkyl, $C_{3-7}$cycloalkyl or aryl; or $R^3$ and $R^4$ taken together form a bivalent radical —$R^3$—$R^4$— of formula:

(a)

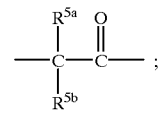

(b)

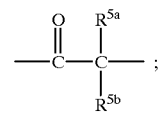

(c)

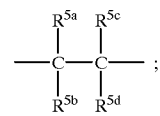

(d)

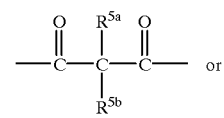

(e)

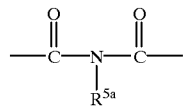

wherein $R^{5a}$, $R^{5b}$, $R^{5c}$, $R^{5d}$ each independently are hydrogen, $C_{1-6}$alkyl or aryl; and aryl is optionally substituted phenyl; as antifungals; their preparation, compositions containing them and their use as a medicine.

14 Claims, No Drawings

2,4,4-TRISUBSTITUTED-1,3-DIOXOLANE ANTIFUNGALS

CROSS REFERENCE TO RELATED APPLICATIONS

This application is a National Stage application under 35 U.S.C. 371 of PCT/EP98/04194 filed Jul. 7, 1998, which claims priority from EP 97.202.181.0, filed Jul. 11, 1997.

The present invention is concerned with novel 2,4,4-trisubstituted-1,3-dioxolane antifungals and their preparation; it further relates to compositions comprising them, as well as their use as a medicine.

EP-A-0,118,138 discloses 2,2,4-trisubstituted-1,3-dioxolanes having antimicrobial properties and effective in inhibiting the growth of *Candida albicans*. The compounds of the present invention differ therefrom structurally by the substitution pattern on the 1,3-dioxolane ring.

WO 88/05048 discloses 2,4,4-trisubstituted-1,3-dioxolane derivatives which are taught to have antifungal activity. The present compounds differ therefrom structurally by the nature of the substituent on the 4-(4-phenylpiperazinyl)phenoxymethyl moiety in the 2 position of the 1,3-dioxolane ring.

The present compounds are found to be active against a wide variety of fungi, in particular against dermatophytes.

The present invention concerns novel compounds of formula

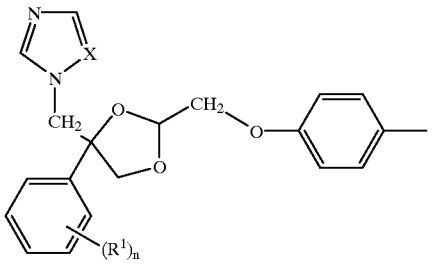

(I)

the N-oxide forms, the pharmaceutically acceptable acid addition salts and stereochemically isomeric forms thereof, wherein n is zero, 1, 2 or 3;

X is N or CH;

each $R^1$ independently is halo, nitro, cyano, amino, hydroxy, $C_{1-4}$alkyl, $C_{1-4}$alkyloxy or trifluoromethyl;

$R^2$ is hydrogen; $C_{3-7}$alkenyl; $C_{3-7}$alkynyl; aryl; $C_{3-7}$cycloalkyl; $C_{1-6}$alkyl or $C_{1-6}$alkyl substituted with hydroxy, $C_{1-4}$alkyloxy, $C_{3-7}$cycloalkyl or aryl;

$R^3$ and $R^4$ each independently are hydrogen, $C_{1-6}$alkyl, $C_{3-7}$cycloalkyl or aryl; or $R^3$ and $R^4$ taken together form a bivalent radical —$R^3$—$R^4$— of formula:

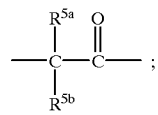 (a)

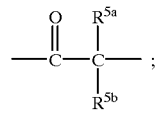 (b)

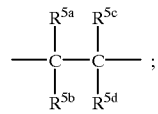 (c)

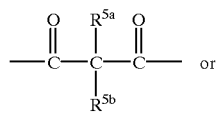 or (d)

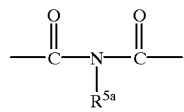 (e)

wherein $R^{5a}$, $R^{5b}$, $R^{5c}$, $R^{5d}$ each independently are hydrogen, $C_{1-6}$alkyl or aryl; and aryl is phenyl or phenyl substituted with one, two or three substituents selected from halo, nitro, cyano, amino, hydroxy, $C_{1-4}$alkyl, $C_{1-4}$alkyloxy or trifluoromethyl.

In the definitions hereinabove and hereinafter the term halo defines fluoro, chloro, bromo and iodo; $C_{1-4}$alkyl defines straight and branched chain saturated hydrocarbon radicals having from 1 to 4 carbon atoms such as, for example, methyl, ethyl, propyl, 1-methylethyl, butyl, 2-butyl, 2-methylpropyl, 2,2-dimethylethyl and the like; $C_{1-6}$alkyl is meant to include $C_{1-4}$alkyl and the higher homologues thereof having 5 or 6 carbon atoms such as, for example, pentyl, 2-methylbutyl, hexyl, 2-methylpentyl and the like; $C_{3-6}$alkyl defines straight and branched chain saturated hydrocarbon radicals having from 3 to 6 carbon atoms such as, for example, propyl, 1-methylethyl, butyl, 2-methylpropyl, 2,2-dimethylethyl, pentyl, 2-methylbutyl, hexyl, 2-methylpentyl and the like; $C_{3-7}$alkenyl defines straight or branched hydrocarbon radicals having one double bond and having from 3 to 7 carbon atoms such as, for example, 2-propenyl, 3-butenyl, 2-butenyl, 2-pentenyl, 3-methyl-2-butenyl, 2-hexenyl, 2-heptenyl and the like, and the carbon atom of said $C_{3-7}$alkenyl being connected to the nitrogen atom preferably is saturated; $C_{3-7}$alkynyl defines straight or branched hydrocarbon radicals having one triple bond and having 3 to 7 carbon atoms such as, for example, 2-propynyl, 3-butynyl, 2-butynyl, 2-pentynyl, 3-methyl-2-butynyl, 2-hexynyl, 2-heptynyl and the like, and the carbon atom of said $C_{3-7}$alkenyl being connected to the nitrogen atom preferably is saturated; $C_{3-7}$cycloalkyl is generic to cyclopropyl, cyclobutyl, cyclopentyl, cyclohexyl and cycloheptyl.

The pharmaceutically acceptable acid addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The term addition salt also comprises the hydrates and solvent addition forms which the compounds of formula (I) are able to form. Examples of such forms are e.g. hydrates, alcoholates and the like.

The N-oxide forms of the present compounds are meant to comprise the compounds of formula (I) wherein one or several nitrogen atoms are oxidized to the so-called N-oxide.

Whenever used hereinafter, the term "compounds of formula (I)" is meant to also include their N-oxide forms, their pharmaceutically acceptable acid addition salts, and their stereochemically isomeric forms.

An interesting group of compounds are those compounds of formula (I) for which one or more of the following conditions apply:

1) n is 1 or 2;
2) $R^1$ is halo;
3) $R^2$ is $C_{3-7}$cycloalkyl or $C_{1-6}$alkyl;
4) $R^3$ is hydrogen or $C_{1-6}$alkyl and $R^4$ is hydrogen or $C_{1-6}$alkyl; or $R^3$ and $R^4$ form a bivalent radical —$R^3$—$R^4$— of formula (a), (b), (c), (d) or (e), wherein $R^5$ is hydrogen or $C_{1-6}$alkyl.

Interesting compounds are those compounds of formula (I) wherein n is 1 or 2 and each $R^1$ independently is halo, and more in particular, wherein n is 2 and both $R^1$ are fluoro, especially when the fluor atoms are attached in the 2- and 4-position of the phenyl ring.

Also interesting are those compounds of formula (I) wherein X is N.

Other interesting compounds are those compounds of formula (I) wherein $R^3$ and $R^4$ form a bivalent radical —$R^3$—$R^4$— of formula (a), (b), (c), (d) or (e) wherein $R^{5a}$, $R^{5b}$, $R^{5c}$ and $R^{5d}$ each independently are hydrogen or $C_{1-6}$alkyl, in particular, —$R^3$—$R^4$— is a radical of formula (c) wherein both $R^{5a}$ and $R^{5b}$ are hydrogen and $R^{5c}$ and $R^{5d}$ are each independently hydrogen or $C_{1-6}$alkyl; or a radical of formula (d) wherein both $R^{5a}$ and $R^{5b}$ are $C_{1-6}$alkyl; or a radical of formula (e) wherein $R^{5a}$ is $C_{1-6}$alkyl.

Yet another interesting group of compounds are those compounds of formula (I) wherein $R^2$ is $C_{3-7}$cycloalkyl or $C_{1-6}$alkyl, in particular wherein $R^2$ is $C_{1-6}$alkyl, preferably wherein $R^2$ is $C_{3-6}$alkyl whereby the alkyl chain is branched in the α position. Said preferred alkyl chains include for example 1-methylethyl and 1-methylpropyl.

A preferred group of compounds are those compounds of formula (I) wherein the phenyl ring attached in the 4-position of the 1,3-dioxolane ring is a 2,4-difluorophenyl ring; and $R^3$ and $R^4$ form a bivalent radical —$R^3$—$R^4$— of formula (c) wherein both $R^{5a}$ and $R^{5b}$ are hydrogen and $R^{5c}$ and $R^{5d}$ are both hydrogen or are both $C_{1-6}$alkyl; and $R^2$ is $C_{1-6}$alkyl.

Also preferred are those compounds of formula (I) wherein the substituents on the 1,3-dioxolane ring have a cis configuration, especially the enantiomerically pure cis isomers.

More preferred are those compounds of formula (I) wherein the phenyl ring attached in the 4-position of the 1,3-dioxolane ring is a 2,4-difluorophenyl ring; and $R^3$ and $R^4$ form a bivalent radical —$R^3$—$R^4$— of formula (c) wherein $R^{5a}$, $R^{5b}$, $R^{5c}$ and $R^{5d}$ are hydrogen; and $R^2$ is methyl, ethyl, propyl, butyl, 1-methylethyl or 1-methylpropyl, especially 1-methylethyl.

Most preferred are 1-[4-[4-[4-[[4-(2,4-difluorophenyl)-4-(1H-1,2,4-triazol-1-ylmethyl)-1,3-dioxolan-2-yl]methoxy] phenyl]-1-piperazinyl]phenyl]-3-(1-methylethyl)-2-imidazolidinone; the N-oxide forms, the pharmaceutically acceptable acid addition salts and stereochemically isomeric forms thereof.

In the following paragraphs there are described different ways of preparing the compounds of formula (I). In order to simplify the structural formulae of the compounds of formula (I) and the intermediates intervening in their preparation, the 2,4,4-trisubstituted moiety will be represented by the symbol T hereinafter.

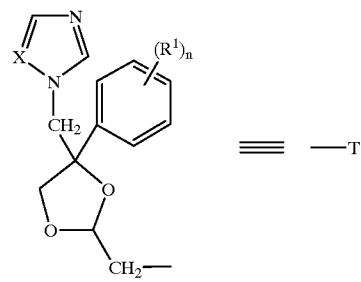

The compounds of formula (I) can conveniently be prepared by O-alkylating an appropriately substituted phenol of formula (III) with an alkylating reagent of formula (II). In formula (II) and hereinafter, W represents an appropriate reactive leaving group such as, for example, halo or a sulfonyloxy group.

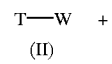

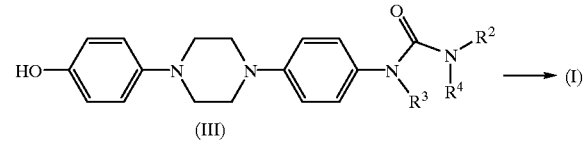

Said O-alkylation reaction can conveniently be conducted in a suitable reaction-inert solvent in the presence of an appropriate base and optionally under an inert atmosphere such as, for example, oxygen-free argon or nitrogen gas. Suitable solvents are, for example, hydrocarbons, halogenated hydrocarbons, alkanols, ethers, ketones, esters, dipolar aprotic solvents or a mixture of such solvents. The acid which is liberated during the course of the reaction may be picked up by an appropriate base such as, for example, sodium carbonate, potassium carbonate, sodium hydroxide, sodium hydride and the like; or an amine, e.g., triethylamine. In some instances it may be advantageous to convert the substituted phenol (III) first into a metal salt thereof, e.g. the sodium salt, by the reaction of (III) with a metal base such as, for example, sodium hydride and the like, and to use said metal salt subsequently in the reaction with (II). The reaction mixture may be stirred and heated in order to enhance the rate of the reaction.

In this and the following preparations, the reaction products may be isolated from the medium and, if necessary, further purified according to methodologies generally known in the art such as, for example, extraction, crystallization, trituration and chromatography.

Alternatively, said O-alkylation may be carried out by applying art-known conditions of phase transfer catalysis reactions. Said conditions comprise stirring the reactants, with an appropriate base and optionally under an inert atmosphere as defined hereinabove, in the presence of a suitable phase transfer catalyst. Somewhat elevated temperatures may be appropriate to enhance the rate of the reaction.

The compounds of formula (I) may also be prepared by transacetalating an acetal of formula (V) with a 1,2-diol of formula (IV) by stirring the reactants in an appropriate reaction-inert solvent in the presence of a suitable acid catalyst.

Said cyclization reaction can conveniently be carried out by mixing the reactants, optionally in a reaction-inert solvent such as, for example, water, an aromatic solvent, a alkanol, a ketone, an ester, an ether, a dipolar aprotic solvent or a mixture of such solvents. The addition of an appropriate base such as, for example, sodium carbonate, sodium hydrogen carbonate, potassium carbonate, sodium hydroxide, calcium oxide, sodium acetate, sodium methoxide, sodium hydride, sodium amide and the like, or an organic base such as, for example, triethylamine, may optionally be used to pick up the acid which is formed during the course of the reaction. In some instances the addition of an iodide salt, e.g. potassium iodide; or a crown ether, e.g. 1,4,7,10,13,16-hexa-

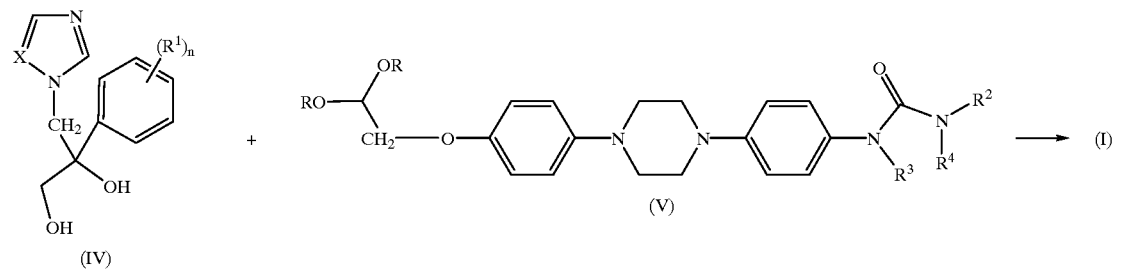

In formula (V) and hereinafter, each R independently represents an alkyl group or both radicals taken together may also form a bivalent alkanediyl radical such as, for example, 1,2-ethanediyl, 1,3-propanediyl, 2,2-dimethyl-1,3-propanediyl and the like. Suitable acid catalysts are for example, hydrochloric and hydrobromic acid, sulfuric acid and the like, or a sulfonic acid. Appropriate reaction inert solvents are, for example, aromatic hydrocarbons, halogenated hydrocarbons, ethers or a mixture thereof. Said transacetalation reaction can conveniently be conducted at temperatures ranging from about 0° C. to about room temperature. In some instances however, the reaction may be conducted at a somewhat elevated temperature, in order to shift the equilibria towards the acetal of formula (I). The alcohol or diol which is liberated during the course of the transacetalation reaction may be removed from the reaction mixture following art-known procedures such as, for example destillation.

The compounds of formula (I) may also be obtained by cyclizing an intermediate of formula (VI) or (IX) with respectively an amine of formula (VII) or (VIII).

oxacyclooctadecane, may be appropriate. Stirring and somewhat elevated temperatures may enhance the rate of the reaction.

The compounds of formula (I) may also be obtained by N-alkylating a compound of formula (X) with an alkylating reagent of formula $R^2$—W (XI) wherein $R^2$ and W are as defined hereinabove.

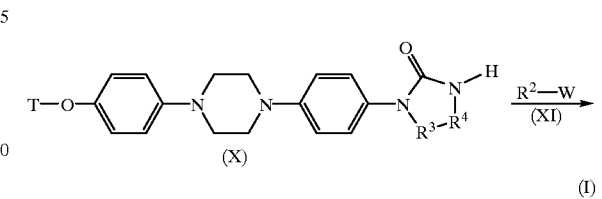

The compounds of formula (I) wherein $R^4$ is hydrogen, said compounds being represented by formula (I-a), can be prepared by reacting an intermediate of formula (XVII) with

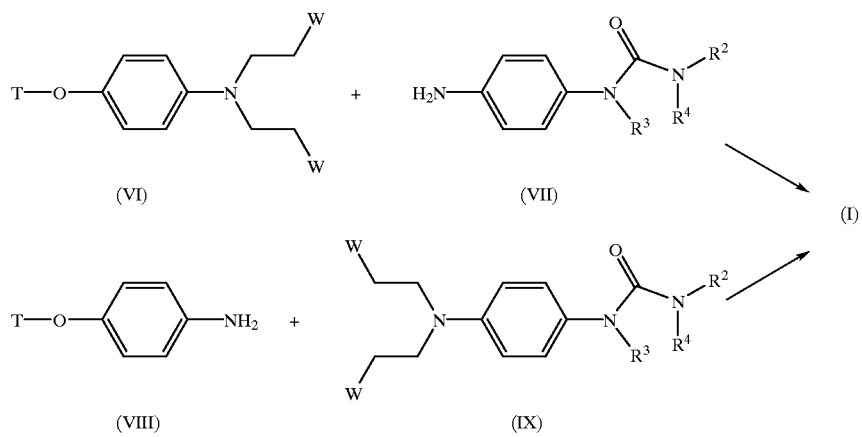

an isocyanate $R^2$—N=C=O in a reaction-inert solvent such as, for example, dichloromethane.

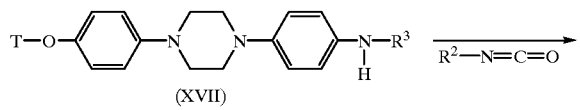

(XVII)

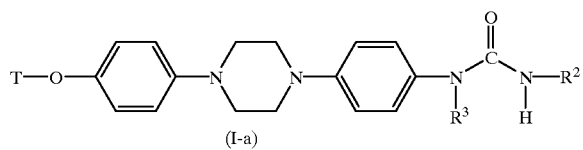

(I-a)

Compounds of formula (I) wherein $R^4$ is selected from hydrogen, $C_{1-6}$alkyl, $C_{3-7}$cycloalkyl and aryl, said $R^4$ being represented by $R^{4'}$ and said compounds being represented by formula (I-b), can be prepared by reacting an intermediate of formula (XVIII) wherein L is a suitable leaving group such as, for example, phenoxy, trichloromethoxy, chloro or imidazolyl, with an intermediate $NHR^2R^{4'}$ in a reaction-inert solvent such as, for example, tetrahydrofuran or dichloromethane, and in the presence of an appropriate base such as, for example, triethylamine. Reactive amino groups in $R^2$, in case they are present, are protected with a protective group P such as, for example, a $C_{1-4}$alkyloxycarbonyl group. Suitably, the reactive amino group may then be deprotected using art-known deprotection techniques to arrive at the desired compound of formula (I-b).

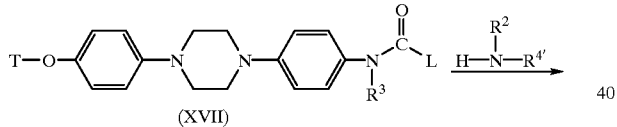

(XVII)

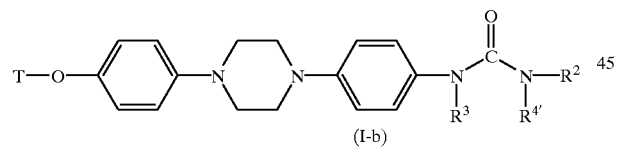

(I-b)

The compounds of formula (I) may also be converted into each other following art-known transformations.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

A number of intermediates and starting materials used in the foregoing preparations are known compounds, while others may be prepared according to art-known methodologies of preparing said or similar compounds. The preparation of the intermediates (II) is described in WO88/05048; the preparation of (III), (VII) and (IX), is described in U.S. Pat. No. 4,619,931, U.S. Pat. No. 4,861,879 and/or EP-A-0,331,232.

In particular, the intermediates of formula (II) can be prepared from intermediates of formula (IV) and acetals of formula (XII), following the transacetalization procedures described hereinabove for the preparation of the compounds of formula (I) from (IV) and (V). The diastereoselectivity of the acetalization can be enhanced in favor of the cis stereoisomer in case W represents a hydroxy moiety.

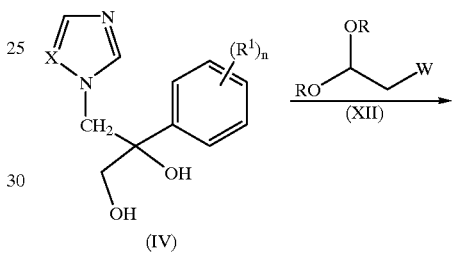

(IV)

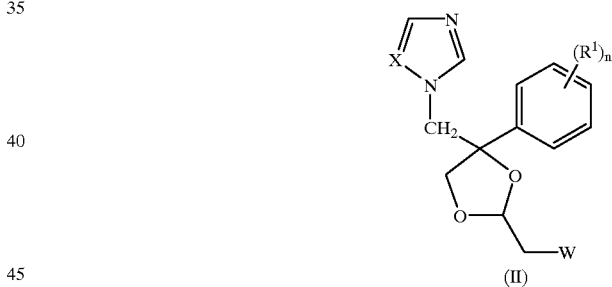

(II)

The intermediates of formula (IV) can be obtained from an acetal (XIII) by N-alkylation with 1H-imidazole or 1,2,4-triazole, followed by hydrolysis of the acetal (XIV) in an acidic aqueous medium. Alternatively, the hydrolysis of the acetal (XIII) may be performed prior to the N-alkylation with 1H-imidazole or 1,2,4-triazole.

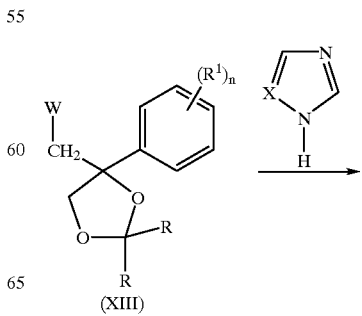

(XIII)

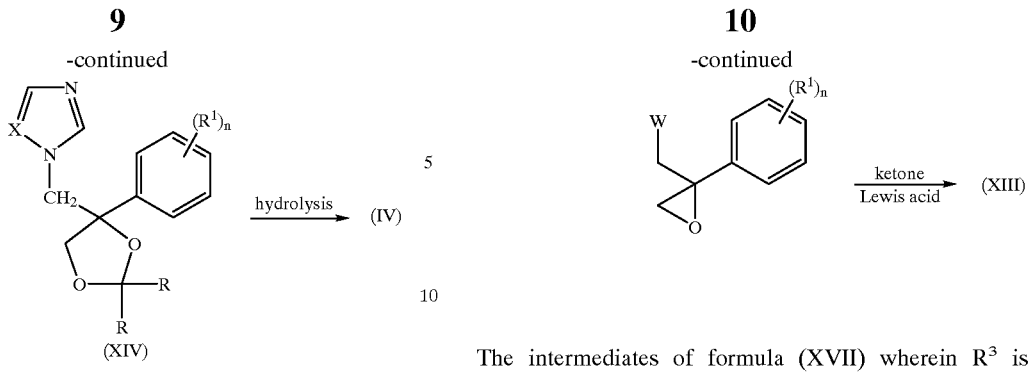

The intermediate (XIII) in turn can be prepared from a 2-propanone derivative of formula (XV) by treatment with an appropriately substituted Grignard reagent of formula (XVI) followed by base-induced epoxide formation and acetalation with a ketone in the presence of a Lewis acid such as, for example, tin(IV) chloride.

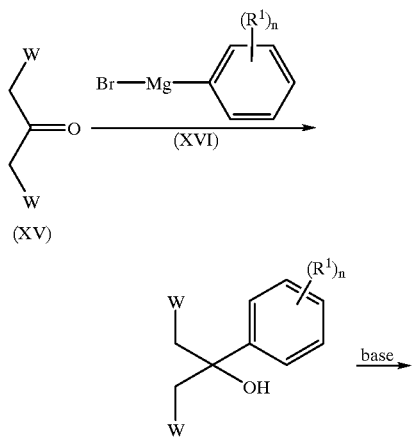

The intermediates of formula (XVII) wherein $R^3$ is hydrogen, said intermediates being represented by formula (XVII-a), can be prepared by reacting an intermediate of formula (XIX-a) wherein $NP_2$ is a protected amino group wherein P is for example a $C_{1-4}$alkyloxycarbonyl group, or a functional derivative of $NP_2$ such as, for example, a nitro group, with an intermediate of formula (II) analogous to the procedure described for the reaction of intermediate (II) with intermediate (III). The thus obtained intermediates of formula (XIX-b) may be deprotected according to art-known deprotection techniques. In case $NP_2$ is a nitro group, art-known reduction techniques such as, for example, reduction using hydrogen in the presence of a catalyst, e.g. palladium on activated carbon, may be used to obtain intermediates of formula (XVII-a). Intermediates of formula (XVII) wherein $R^3$ is $C_{1-6}$alkyl, $C_{3-7}$cycloalkyl or aryl, said $R^3$ represented by $R^{3'}$ and said intermediates being represent by formula (XVII-b), can be prepared by reacting an intermediate of formula (XVII-a) with an intermediate W—$R^{3'}$ or, in case $R^{3'}$ is methyl, a functional derivative thereof such as paraformaldehyde together with sodium methanolate, in a reaction-inert solvent such as, for example, methanol, and in the presence of a suitable reducing agent such as, for example, sodiumborohydride.

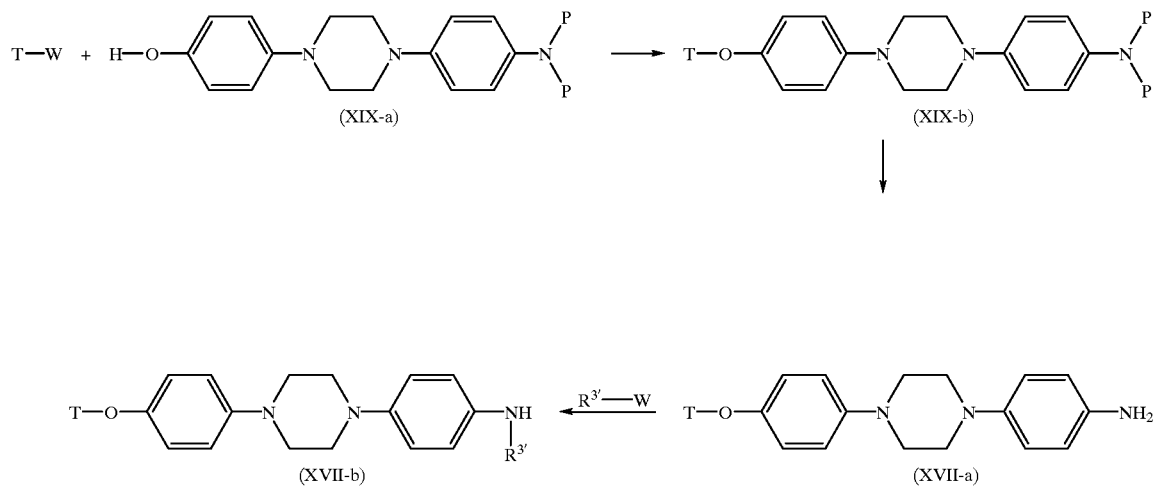

Intermediates of formula (XVIII) can be prepared by reacting an intermediate of formula (XVII) with a chloroformate such as, for example, phenylchloroformate or trichloromethylchloroformate, bis(trichloromethyl) carbonate, or with a functional derivative thereof such as, for example, 1,1'-carbonylbis-1H-imidazole.

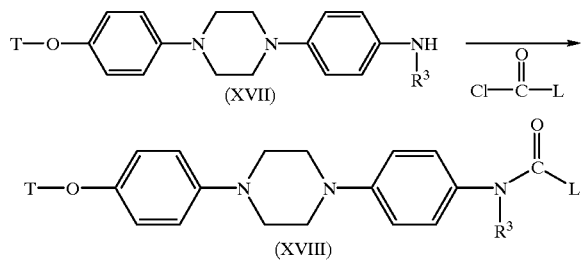

It may be convenient to prepare the intermediates of formula (XVIII) and the subsequent compounds of formula (I-b) in the same reaction mixture.

The term "stereochemically isomeric forms" as used hereinbefore defines all the possible isomeric forms which the compounds of formula (I) may possess. From formula (I) it is evident that the compounds of this invention have at least two asymmetric carbon atoms in their structures, namely those located in the 2- and 4-position of the dioxolane nucleus. Depending on the nature of the substituents $R^1$ to $R^5$, the compounds of formula (I) may also contain a third or more asymmetric carbon atoms. Consequently the compounds of formula (I) can exist under different stereochemically isomeric forms. Unless otherwise mentioned or indicated, the chemical designation of compounds denotes the mixture of all possible stereo-chemically isomeric forms, said mixtures containing all diastereoisomers and enantiomers of the basic molecular structure.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

The absolute configuration of each asymmetric center may be indicated by the stereochemical descriptors R and S, this R and S notation corresponding to the rules described in Pure Appl. Chem. 1976, 45, 11–30. The terms cis and trans are used herein in accordance with Chemical Abstracts nomenclature (J. Org. Chem. 1970, 35 (9), 2849–2867), and refer to the position of the substituents on a ring moiety, more in particular on the dioxolane ring in the compounds of formula (I). For instance, when establishing the cis or trans configuration of the dioxolane ring, the substituent with the highest priority on the carbon atom in the 2 position of the dioxolane ring, and the substituent with the highest priority on the carbon atom in the 4 position of the dioxolane ring are considered (the priority of a substituent being determined according to the Cahn-Ingold-Prelog sequence rules). When said two substituents with highest priority are at the same side of the ring then the configuration is designated cis, if not, the configuration is designated trans.

For instance, the absolute configuration of the asymmetric carbon atoms of compound 51 as described in example B.3 hereinafter, i.e. (2S-cis)-1-[4-[4-[4-[[4-(2,4-difluorophenyl)-4-(1H-1,2,4-triazol-1-ylmethyl)-1,3-dioxolan-2-yl]methoxy]phenyl]-1-piperazinyl]phenyl]-3-(1-methylethyl)-2-imidazolidinone, is as depicted hereinbelow. Thus, carbon atom number 2 of the dioxolane ring in this compound has the S configuration and carbon number 4 has the R configuration.

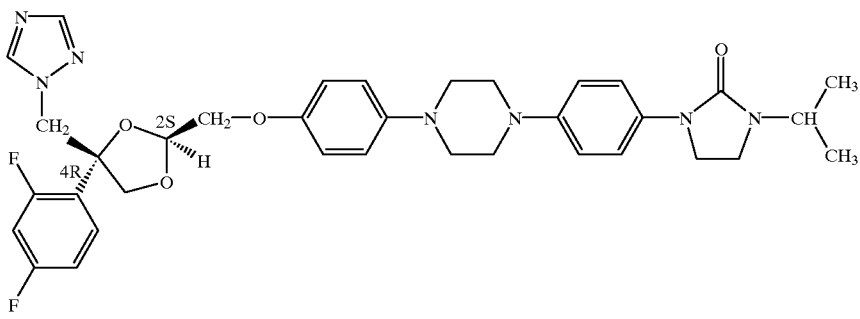

2S-cis

Pure stereoisomeric forms of the compounds and the intermediates of this invention may be obtained by the application of art-known procedures. For instance, enantiomers may be separated from each other by the selective crystallization of their diastereomeric salts with optically active acids. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials. Stereochemically isomeric forms of the compounds of formula (I) are obviously intended to be included within the scope of the invention.

The diastereomeric racemates of (I) can be obtained separately by conventional methods. Appropriate physical separation methods which may advantageously be employed are, for example, selective crystallization and chromatography, e.g., column chromatography.

Since the stereochemical configuration is already fixed in a number of intermediate compounds, e.g., in the intermediates of formulae (II), (VI), (VIII) and (X) and some of their respective precursors, it is also possible to separate cis and trans forms at one of these stages. The separation of cis and trans forms of such intermediates may be performed by conventional methods as mentioned hereinabove for the separation of the cis and trans forms of the compounds of formula (I). The corresponding diastereomeric forms of (I) may then be derived therefrom in the previously indicated manner.

It is evident that the cis and trans racemates may be further resolved into their optical isomers, cis(+) and cis(−), respectively trans(+) and trans(−) by the application of art-known methodologies. In case additional asymmetric centra are present in the abovementioned intermediates and/or compounds, the resulting mixtures of stereoisomers may be further separated by the previously indicated methodologies. Preferably, if a specific stereochemical form is desired, said compound will be synthesized by stereoselective methods of preparation, which will advantageously employ enantiomerically pure starting materials.

The compounds of formula (I), the pharmaceutically acceptable addition salts and the stereochemically isomeric forms thereof are useful agents for combating fungi in vivo. The present compounds are found to be active against a wide variety of fungi, such as Candida spp., e.g. *Candida albicans, Candida glabrata, Candida krusei, Candida parapsilosis, Candida kefyr, Candida tropicalis*; Aspergillus spp., e.g. *Aspergillus fumigatus, Aspergillus niger, Aspergillus flavus; Cryptococcus neoformans; Sporothrix schenckii; Epidermophyton floccosum; Microsporum canis*; Trichophyton spp., e.g. *Trichophyton mentagrophytes, Trichophyton rubrum, Trichophyton quinckeanum*; and several dematiaceous hyphomycetes.

The compounds of the present invention show enhanced antifungal activity against some fungal isolates and have a good oral availability. In vitro experiments such as the determination of fungal susceptibility of the present compounds for, for instance, Candida and dermatophyte isolates, and the determination of the effects of the present compounds on the sterol synthesis in, for instance, *Candida albicans* and *Trichophyton mentagrophytes*, demonstrate their antifungal potency. Also in vivo experiments in several mouse, guinea-pig and rat models, for instance, oral administration of a test compound to mice infected with *Trichophyton quinckeanum* or *Microsporum canis*, show that the present compounds are potent antifungals. The example hereinbelow demonstrates the in vitro antifungal activity of the present compounds versus *Candida kefyr* and *Trichophyton rubrum*.

In view of the utility of the compounds of formula (I), there is provided a method of treating warm-blooded animals, including humans, suffering from fungal infections. Said method comprises the systemic administration of an effective amount of a compound of formula (I), a N-oxide form, a pharmaceutically acceptable addition salt or a possible stereoisomeric form thereof, to warm-blooded animals, including humans. Hence, compounds of formula (I) are provided for use as a medicine, in particular, the use of a compound of formula (I) in the manufacture of a medicament useful in treating fungal infections is provided.

In general, it is contemplated that a therapeutically effective daily amount would be from 0.05 mg/kg to 20 mg/kg body weight.

The present invention also provides compositions for treating or preventing fungal infections comprising a therapeutically effective amount of a compound of formula (I) and a pharmaceutically acceptable carrier or diluent.

In view of their useful pharmacological properties, the subject compounds may be formulated into various pharmaceutical forms for systemic or topical administration purposes.

To prepare the pharmaceutical compositions of this invention, a therapeutically effective amount of a particular compound, in base or addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection.

For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. As appropriate compositions for topical application there may be cited all compositions usually employed for topically administering drugs e.g. creams, gel, dressings, shampoos, tinctures, pastes, ointments, salves, powders and the like. In particular, the present compounds may be formulated in topical compositions specially adapted for delivery to the nail. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. For parenteral compositions, the carrier will usually comprise sterile water, at least in large part. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed.

In order to enhance the solubility and/or the stability of the compounds of formula (I) in pharmaceutical compositions, it can be advantageous to employ α-, β- or γ-cyclodextrins or their derivatives. Also co-solvents such as alcohols may improve the solubility and/or the stability of the compounds of formula (I) in pharmaceutical compositions. In the preparation of aqueous compositions, addition salts of the subject compounds are obviously more suitable due to their increased water solubility.

Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxypropyl or hydroxybutyl; carboxy$C_{1-6}$alkyl, particularly carboxymethyl or carboxyethyl; $C_{1-6}$alkylcarbonyl, particularly acetyl; $C_{1-6}$alkyloxycarbonyl$C_{1-6}$alkyl or carboxy-$C_{1-6}$alkyloxy$C_{1-6}$alkyl, particularly carboxymethoxypropyl or carboxyethoxypropyl; $C_{1-6}$alkylcarbonyloxy$C_{1-6}$alkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The M.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. Preferably, as measured by mass spectrometry, the M.S. ranges from 0.125 to 10.

The average substitution degree (D.S.) refers to the average number of substituted hydroxyls per anhydroglucose unit. The D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. Preferably, as measured by mass spectrometry, the D.S. ranges from 0.125 to 3.

An interesting way of formulating the present compounds in combination with a cyclodextrin or a derivative thereof has been described in EP-A-721,337. The formulations described therein are particularly suitable for oral administration and comprise an antifungal as active ingredient, a sufficient amount of a cyclodextrin or a derivative thereof as a solubilizer, an aqueous acidic medium as bulk liquid carrier and an alcoholic co-solvent that greatly simplifies the preparation of the composition. Said formulations may also be rendered more palatable by adding pharmaceutically acceptable sweeteners and/or flavours.

Other convenient ways to enhance the solubility of the compounds of the present invention in pharmaceutical compositions are described in WO-94/05263, PCT application No. PCT/EP98/01773, EP-A-499,299 and WO 97/44014.

More in particular, the present compounds may be formulated in a pharmaceutical composition comprising a therapeutically effective amount of particles consisting of a solid dispersion comprising (a) a compound of formula (I), and (b) one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermo-dynamics, such a solid dispersion is referred to as "a solid solution". Solid solutions are preferred physical systems because the components therein are usually readily bioavailable to the organisms to which they are administered.

The term "a solid dispersion" also comprises dispersions which are less homogenous throughout than solid solutions. Such dispersions are not chemically and physically uniform throughout or comprise more than one phase.

The water-soluble polymer in the particles is a polymer that has an apparent viscosity of 1 to 100 mPa.s when dissolved in a 2% aqueous solution at 20° C. solution.

Preferred water-soluble polymers are hydroxypropyl methylcelluloses or HPMC. HPMC having a methoxy degree of substitution from about 0.8 to about 2.5 and a hydroxypropyl molar substitution from about 0.05 to about 3.0 are generally water-soluble. Methoxy degree of substitution refers to the average number of methyl ether groups present per anhydroglucose unit of the cellulose molecule. Hydroxy-propyl molar substitution refers to the average number of moles of propylene oxide which have reacted with each anhydroglucose unit of the cellulose molecule.

The particles as defined hereinabove can be prepared by first preparing a solid dispersion of the components, and then optionally grinding or milling that dispersion. Various techniques exist for preparing solid dispersions including melt-extrusion, spray-drying and solution-evaporation, melt-extrusion being preferred.

It may further be convenient to formulate the present azole antifungals in the form of nanoparticles which have a surface modifier adsorbed on the surface thereof in an amount sufficient to maintain an effective average particle size of less than 1000 nm. Useful surface modifiers are believed to include those which physically adhere to the surface of the antifungal agent but do not chemically bond to the antifungal agent.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the present compounds involves a pharmaceutical composition whereby the present antifungals are incorporation in hydrophilic polymers and applying this mixture as a coat film over many small beads, thus yielding a composition with good bioavailability which can conveniently be manufactured and which is suitable for preparing pharmaceutical dosage forms for oral administration.

Said beads comprise (a) a central, rounded or spherical core, (b) a coating film of a hydrophilic polymer and an antifungal agent and (c) a seal-coating polymer layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

The cores in said beads may have a diameter of about 60 mesh, corresponding to about 250 μm, or larger. Particular beads having a 25–30 mesh core (600–710 μm) are disclosed in WO-94/05263. PCT/EP98/01773 discloses beads of which the core has a diameter of about 250 to about 600 (30–60 mesh).

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Also, it may be convenient to combine the present antifungal compounds with other antifungals such as, for example, azole containing antifungals, e.g. bifoconazole, crococonazole, clotrimazole, eberconazole, econazole, fenticonazole, fluconazole, flutrimazole, isoconazole, itraconazole, ketoconazole, lanoconazole, miconazole, neticonazole, omoconazole, oxiconazole, saperconazole, SCH 39304, sertaconazole, sulconazole, tioconazole, voriconazole; or non-azole antifungals, e.g. amorolfine, butenafine, ciclopirox, cioteronel, naftidine, isotretinoin, rimoprogin, terbinafine. It is particularly useful to combine the present compounds with other dermatological antifungals.

The combination of an antifungal compound and a compound of formula (I) can be used as a medicine. Thus, the present invention also relates to a product containing (a) a compound of formula (I), and (b) another antifungal compound, as a combined preparation for simultaneous, separate or sequential use in antifungal treatment.

The different drugs in such products may be combined in a single preparation together with pharmaceutically acceptable carriers. Alternatively, such products may comprise, for example, a kit comprising a container with a suitable composition containing a compound of formula (I) and another container with a composition containing another antifungal. Such a product may have the advantage that a physician can select on the basis of the diagnosis of the patient to be treated the appropriate amounts of each component and the sequence and timing of the administration thereof.

The following examples are intended to illustrate the invention.

Experimental Part

Of some compounds of formula (I) the absolute stereochemical configuration of the stereogenic carbon atom(s) therein was not experimentally determined. In those cases the stereochemically isomeric form which was first isolated is designated as "A" and the second as "B", without further reference to the actual stereochemical configuration.

As used hereinafter, "DMF" is defined as N,N-dimethylformamide, "EtOAc" is defined as ethylacetate, "DIPE" is defined as diisopropylether.

A. Preparation of the Intermediates

Example A-1 a) To a stirred and cooled (−78° C.) mixture of 2-chloro-1(2,4-difluorophenyl)-1-ethanone (30 g), chloroiodomethane (56.4 g) and tetrahydrofuran 267 ml) was added dropwise a 6% solution of methyllithium-lithiumbromide complex in diethylether (215 ml). The reaction mixture was slowly warmed to room temperature and was then hydrolysed with $NH_4Cl$. Aqueous NaOH was added and the mixture was stirred for 1 hour. The organic layer was separated, washed, dried, filtered and the solvent evaporated. The residue was purified over silica gel (eluent: hexane/$CH_3COOC_2H_5$ 98/2). The solvent of the desired fraction was evaporated, yielding 11 g (16.8%) of 2-(chloromethyl)-2-(2,4-difluorophenyl)oxirane (interm. 1).

b) A mixture of intermediate (1) (22 g), 2-propanone (158 ml) and a catalytic amount of trifluoro[1,1′-oxybis[ethane]] boron was stirred overnight at room temperature. The reaction mixture was poured into an aqueous $NaHCO_3$ solution and the product was extracted with $CH_2Cl_2$. The extract was washed with water, dried, filtered and the solvent was evaporated. The residue was purified over silica gel (eluent:hexane). The solvent of the desired fraction was evaporated, yielding 21 g (74.3%) of 4-(chloromethyl)-4-(2,4-difluorophenyl)-2,2-dimethyl-1,3-dioxolane (interm. 2).

In a similar manner were prepared:

4-(chloromethyl)-4-(4-fluorophenyl)-2,2-dimethyl-1,3-dioxolane (interm. 3); and 4-(chloromethyl)-4-(4-chlorophenyl)-2,2-dimethyl-1,3-dioxolane (interm. 4).

Example A-2 a) A mixture of intermediate (2) (55 g), methanol (395 ml), water (100 ml) and hydrochloric acid (6.35 ml) was stirred overnight at reflux temperature. After cooling, the reaction mixture was neutralized with $NaHCO_3$ and the solvent was evaporated. The residue was taken up in ethyl acetate and this solution was washed with NaCl, dried, filtered and the solvent was evaporated, yielding 45 g (96.5%) of 3-chloro-2-(2,4-difluorophenyl)-1,2-propanediol (interm. 5).

b) A mixture of 1H-1,2,4-triazole (1.37 g), a dispersion of sodium hydride in mineral oil (50%) (0.6 ml) and DMF (47 ml) was stirred for 3 hours at 80° C. Intermediate (5) was added (1.5 g) and the mixture was stirred at 80° C. for 1 hour. The solvent was evaporated and the residue was purified by over silica gel ($CHCl_3$/$CH_3OH$ 98/2). The solvent of the desired fraction was evaporated, yielding 0.7 g (40.9%) of 2-(2,4-difluorophenyl)-3-(1H-1,2,4-triazol-1-yl)-1,2-propanediol (interm. 6; mp. 132.3° C.).

c) A mixture of intermediate (6) (0.16 mol) in methanesulfonic acid (100 ml) and $CH_2Cl_2$ (1000 ml) was stirred on an ice bath. 1-bromo-2,2-diethoxyethane (0.2 mol) was added dropwise at 10° C. The mixture was allowed to warm to room temperature, stirred overnight, poured out into a saturated aqueous $NaHCO_3$ solution and extracted with $CH_2Cl_2$. The organic layer was separated, dried, filtered and the solvent was evaporated. The residue was purified over silica gel (eluent: $CH_2Cl_2$/$CH_3OH$ from 100/0 to 98/2). The desired fractions were collected and the solvent was evaporated. This residue was combined with the residue obtained from the same reaction performed seperately. This combined residue was further purified and separated into its enantiomers by chiral column chromatography over Chiralcel OD (eluent: hexane/ethanol 75/25). The pure fraction groups were collected and their solvent was evaporated, yielding 45.4 g of (2R-cis)-1-[[2-(bromomethyl)-4-(2,4-difluorophenyl)-1,3-dioxolan-4-yl]methyl]-1H-1,2,4-triazole; $\alpha_{20}^D$=−4.26° (c=28.2 mg/3 ml in DMF) (interm. 7) and 36.3 g (2S-cis)-1-[[2-(bromomethyl)-4-(2,4-difluorophenyl)-1,3-dioxolan-4-yl]methyl]-1H-1,2,4-triazole; $\alpha_{20}^D$=+5.83° (c =16.46 mg/2 ml in DMF) (interm. 8).

Example A-3 a) To a stirred mixture of a sodium hydride dispersion 50% in diethylether (25 ml) and DMF (900 ml) was added dropwise a solution of 1H-1,2,4-triazole (40 g) in DMF (225 ml). Stirring was continued for 3 hours at 60° C. A solution of intermediate (3) (50 g) in DMF (225 ml) was added dropwise at 130° C. and the mixture was stirred overnight. The solvent was evaporated and the residue was purified over silica gel (eluent: $CHCl_3$/$CH_3OH$ 98/2). The pure fractions were collected and the solvent was evaporated, yielding 38 g (68.5%) of 1-[[4-(4-fluorophenyl)-2,2-dimethyl-1,3-dioxolan-4-yl]methyl]-1H-1,2,4-triazole (interm. 9).

b) A mixture of intermediate (9) (38 g), methanol (320 ml), water (200 ml) and concentrated hydrochloric acid (60 ml) was stirred overnight at reflux temperature. After cooling, the reaction mixture was poured into an aqueous $NaHCO_3$ solution. The solvent was evaporated and the residue was stirred in ethyl acetate. The precipitate was filtered off and the filtrate was dried, filtered and evaporated, yielding 25.5 g (78.4%) 2-(4-fluorophenyl)-3-(1H-1,2,4-triazol-1-yl)-1,2-propanediol (interm. 10).

c) A mixture of intermediate (10) (25 g), 2-bromo-1,1-diethoxyethane (20.6 g) and methanesulfonic acid (225 g) was stirred for 2 hours at room temperature. The reaction mixture was added dropwise to an aqueous $NaHCO_3$ solution. The mixture was extracted with $CHCl_3$. The extract was washed with water, dried, filtered and the solvent evaporated. The residue was purified over silica gel (eluent: $CHCl_3$/ethyl acetate/hexane 50/30/20). The desired fraction was collected and the solvent was evaporated. The residue was converted into the hydrochloride salt in 4-methyl-2-pentanone. The salt was filtered off and dried, yielding 7 g (17.6%) cis-1-[[2-(bromomethyl)-4-(4-fluorophenyl)-1,3-dioxolan-4-yl]methyl]-1H-1,2-4-triazole monohydrochloride (interm. 11).

In a similar manner were prepared:

cis-1-[[2-(bromomethyl)-4-(4-chlorophenyl)-1,3-dioxolan-4-yl]methyl]-1H-1,2,4-tirazole (interm. 12);

cis-1-[[2-(bromomethyl)-4-(2,4-dichlorophenyl)-1,3-dioxolan-4-yl]methyl]-1H-1,2,4-triazole (interm. 13);

cis-1-[[2-(bromomethyl)-4-(4-chlorophenyl)-1,3-dioxolan-4-yl]methyl]-1H-imidazole (interm. 14); and cis-1-[[2-(bromomethyl)-4-(4-fluorophenyl)-1,3-dioxolan-4-yl]methyl]-1H-imidazole (interm. 15).

Example A-4 a) 2,2-Dimethylmalonyl chloride (0.057 mol) was added to a solution of N-[4-[4-(4-methoxyphenyl)-1-piperazinyl]phenyl]urea (0.057 mol) in tetrahydrothiophene, 1,1-dioxide (200 ml). After stirring for 15 minutes, the reaction mixture was heated to 40° C. for 3 hours and at 50° C. for 2 hours. The reaction mixture was allowed to stand overnight at 25° C. The product was precipitated with diethyl ether and crystallized by trituration. The product was recrystallized from 2-propanol, yielding 20.1 g of 1-[4-[4-(4-methoxyphenyl)-1-piperazinyl)phenyl]- 5,5-dimethyl-2,4,6 (1H,3H,5H)-pyrimidinetrione (interm. 16).

b) NaH 80% (0.0174 mol) was washed free of oil with hexane. DMF (70 ml) was added under argon atmosphere. Intermediate (16) (0.0166 mol) was added and the mixture was stirred for 30 minutes. Iodoethane (0.0182 mol) was added and the mixture was heated for 3 hours at 80–90° C. The reaction mixture was poured out into water and the product was extracted with $CH_2Cl_2$. The extract was dried and the solvent evaporated. The residue was purified over basic $Al_2O_3$ (eluent: $CH_2Cl_2$). The pure fraction was collected and the solvent was evaporated. The residue was crystallized from acetonitrile, yielding 3.0 g of 1-ethyl-3-[4-[4-(4-methoxyphenyl)-1-piperazinyl]phenyl]-5,5-dimethylpyrimidine-2,4,6(1H,3H,5H)trione (interm. 17).

c) A solution of intermediate (17) (0.0068 mol) in HBr (60 ml; 48%) and acetic acid (30 ml) was refluxed for 5 hours. The reaction mixture was poured into a $K_2CO_3$ solution and the product was extracted with $CH_2Cl_2$. The extract was dried, filtered and the solvent evporated. The residue was crystallized from acetonitrile, 2-propanone and further purified over silica gel (eluent: $CH_3OH/CH_2Cl_2$ 2/98). The residue was crystallized from acetonitrile, yielding 1.2 g (40%) of 1-ethyl-3-[4-[4-(4-hydroxyphenyl)-1-piperazinyl]phenyl]-5,5-dimethylpyrimidine-2,4,6(1H,3H,5H)trione (interm. 18).

Example A.5 a) A mixture of intermediate 8 (0.048 mol) in 1,3-dimethyl-2-imidazolidinone (200 ml) was stirred under $N_2$ flow for 15 minutes. NaOH (3 ml; 50%) was added. The mixture was stirred for 30 minutes. 4-[4-(4-nitrophenyl)-1-piperazinyl]phenol (0.04 mol) and then NaOH (2.4 g; solid) were added. The mixture was stirred at 70° C. mol under $N_2$ flow for 9 hours and at room temperature overnight, then poured out into $H_2O$ and stirred for 1 hour. The precipitate was filtered off and dissolved in $CH_2Cl_2$. The organic solution was washed, dried, filtered and the solvent was evaporated. The residue was purified by column chromatography over silica gel (eluent: $CH_2Cl_2/CH_3OH$/EtOAc/hexane 48/2/30/20). The pure fractions were collected and the solvent was evaporated. The residue was crystallized from EtOAc. The precipitate was filtered off and dried, yielding 9 g of (2S-cis)-1-[4-[[4-(2,4-difluorophenyl)-4-(1H-1,2,4-triazol-1-ylmethyl)-1,3-dioxolan-2-yl]methoxy]phenyl]-4-(4-nitrophenyl)piperazine (interm. 19).

b) A mixture of intermediate 19 (0.0155 mol) in tetrahydrofuran (250 ml) was hydrogenated at 50° C. with palladium on activated carbon (2 g; 10%) as a catalyst in the presence of thiophene solution (1 ml). After uptake of $H_2$ (3 equiv), the catalyst was filtered off and the filtrate was evaporated. The residue was triturated in 2-propanol. The precipitate was filtered off and dried, yielding 8 g (94%) of (2S-cis)-4-[4-[4-[[4-(2,4-difluorophenyl)-4-(1H-1,2,4-triazol-1-ylmethyl)-1,3-dioxolan-2-yl]methoxy]-phenyl]-1-piperazinyl]benzenamine (interm. 20; mp. 180° C.; $\alpha_{20}^D$=+ 20.45° (c=26.16 mg/5 ml in DMF)).

c) A mixture of intermediate 20 (0.0033 mol), paraformaldehyde (0.0066 mol) and $NaOCH_3$ (0.022 mol) in methanol (50 ml) was stirred and refluxed for 4 hours. $NaBH_4$ (0.008 mol) was added. The mixture was stirred and refluxed for 1 hour and then cooled. $H_2O$ was added. The precipitate was filtered off and dried. The residue was purified over silica gel on a glass filter (eluent: $CH_2Cl_2/CH_3OH$/EtOAc/n-hexane 48/2/30/20). The pure fractions were collected and the solvent was evaporated. The residue was triturated in 2-propanol, filtered off and dried, yielding 1.2 g (64%) of (B-cis)-4-[4-[4-[[4-(2,4-difluorophenyl)-4-(1H-1,2,4-triazol-1-ylmethyl)-1,3-dioxolan-2-yl]methoxy]phenyl]-1-piperazinyl]benzenamine (interm. 21; mp. 181° C.; $\alpha_{20}^D$=+ 20.63° (c=24.96 mg/5 ml in DMF)).

B. Preparation of the Compounds of Formula (I)

Example B.1

A mixture of intermediate 18 (0.0114 mol) in DMF (50 ml) was stirred at room temperature under $N_2$ flow. Sodium bis(trimethylsilyl)amide (0.012 mol) was added. The mixture was stirred for 10 minutes. Intermediate (7) (0.015 mol) was added. The mixture was stirred at 60° C. for 6 hours, then cooled, poured out into $H_2O$ and extracted with $CH_2Cl_2$. The organic layer was separated, washed with $H_2O$, dried, filtered and the solvent was evaporated. The residue was purified by column chromatography over silica gel (eluent: $CH_2Cl_2/CH_3OH/EtOAc/n$-hexane 49/1/30/20 and 47/3/30/20). The pure fractions were collected and the solvent was evaporated. The residue was crystallized from ethanol. The precipitate was filtered off and dried, yielding 2.2 g (2R-cis)-1-ethyl-3-[4-[4-[4-[[4-(2,4-diflurorophenyl)-4-(1H-1,2,4-triazol-1-ylmethyl)-1,3-dioxolan-2-yl]methoxy]phenyl]-1-piperazinyl]phenyl]-5,5-dimethyl-2,4,6 (1H,3H,5H)-pyrimidinetrione (27%); $\alpha_{20}^D = -13.92°$ (c=20.11 mg/2 ml in DMF) (Comp. 48; mp. 126.1° C.).

Example B.2

1-ethyl-3-[4-[4-[(4-hydroxyphenyl)-1-piperazinyl]phenyl]-5-propyl-1,3,5-triazine-2,4,6(1H,3H,5H)-trione (0.011 mol) was dissolved under $N_2$ flow in DMF (40 ml) and toluene (10 ml). Sodium hydride (0.011 mol) was added. The mixture was stirred at room temperature and then added dropwise at 70° C. to a mixture of intermediate (8) (0.015 mol) in DMF (20 ml). The mixture was stirred at 70° C. for 5 hours, then cooled, poured out into water and extracted with $CH_2Cl_2$. The organic layer was separated, washed with water, dried, filtered and the solvent was evaporated. The residue was purified by column chromatography over silica gel (eluent: $CH_2Cl_2/CH_3OH/EtOAc$/hexane 49/1/30/20 and 48/2/30/20). The pure fractions were collected and the solvent was evaporated. The residue was crystallized from ethanol. The precipitate was filtered off and dried, yielding 3.28 g (40%) of (2S-cis)-1-ethyl-3-[4-[4-[4-[[4-(2,4-difluorophenyl)-4-(1H-1,2,4-triazol-1-ylmethyl)-1,3-dioxolan-2-yl]methoxy]-phenyl]-1-piperazinyl]phenyl]-5-propyl-1,3,5-triazine-2,4,6(1H,3H,5H)-trione; $\alpha_{20}^D = +15.73°$ (c=19.96 mg/2 ml in DMF) (Comp. 47; mp. 158.8° C.).

Example B.3 a) A mixture of 1-[4-[4-(4-hydroxyphenyl)-1-piperazinyl]phenyl]-3-(1-methylethyl)-2-imidazolidinone (0.037 mol) and sodium hydroxide (0.165 mol) in DMF (500 ml) was stirred at 50° C. mol under $N_2$ flow for 1 hour. A mixture of intermediate (8) (0.055 mol) in DMF (100 ml) was added dropwise. The mixture was stirred at 50° C. under $N_2$ flow overnight. The solvent was evaporated. The residue was dissolved in $CH_2Cl_2$. The organic solution was washed, dried, filtered and the solvent was evaporated. The residue was purified twice by column chromatography over silica gel (eluent: $CH_2Cl_2$/hexane/EtOAc 50/20/30). The pure fractions were collected and the solvent was evaporated. The residue was triturated in DIPE and EtOAc, filtered off and dried, yielding 14.97 g (62.5%) of (2S-cis)-1-[4-[4-[4-[[4-(2,4-difluorophenyl)-4-(1H-1,2,4-triazol-1-ylmethyl)-1,3-dioxolan-2-yl]methoxy]phenyl]-1-piperazinyl]phenyl]-3-(1-methylethyl)-2-imidazolidinone; $\alpha_{20}^D = +17.54°$ (c=25.37 mg/5 ml in DMF) (Comp. 51; mp. 177.8° C.).

b) Compound 51 (0.0045 mol) was dissolved in boiling 2-propanol (200 ml). HCl in 2-propanol (0.0048 mol) was added and the mixture was concentrated to 100 ml of volume, then allowed to crystallize out. The precipitate was filtered off and dried, yielding 1.5 g (48%) of (2S-cis)-1-[4-[4-[4-[[4-(2,4-difluorophenyl)-4-(1H-1,2,4-triazol-1-ylmethyl)-1,3-dioxolan-2-yl]methoxy]phenyl]-1-piperazinyl]phenyl]-3-(1-methylethyl)-2-imidazolidinone hydrochloride (1:1) (Comp. 52).

Example B.4 cis-1-[4-[4-[4-[[4-(2,4-difluorophenyl)-4-(1H-1,2,4-triazol-1-ylmethyl)-1,3-dioxolan-2-yl]methoxy]phenyl]-1-piperazinyl]phenyl]-3-(1-methylpropyl)-2-imidazolidinone was prepared in a similar manner as described in example B.3 but using additionally a catalytic amount of potassium iodide (Comp. 21; mp. 155.1° C.).

Example B.5

Isopropyl isocyanate (0.008 mol) was added to a stirring mixture of intermediate 20 (0.0055 mol) in $CH_2Cl_2$ (100 ml). The mixture was stirred for 1 hour. Isopropyl isocyanate (0.114 mol) was added again. The mixture was stirred for 4 hours. The solvent was evaporated. The residue was purified by column chromatography over silica gel (eluent: $CH_2Cl_2/CH_3OH$ 99/1 and 98/2). The pure fractions were collected and the solvent was evaporated. The residue was boiled in ethanol. The mixture was cooled. The precipitate was filtered off and dried, yielding 2.6 g (74%) of (2S-cis)-N-[4-[4-[4-[[4-(2,4-difluorophenyl)-4-(1H-1,2,4-triazol-1-ylmetyl)-1,3-dioxolan-2-yl]-methoxy]phenyl]-1-piperazinyl]phenyl]-N'-(1-methylethyl)urea (Comp. 53; mp. 196° C.; $\alpha_{20}^D = +18.64°$ (c=24.68 mg/5 ml in DMF)).

Example B.6 a) 1,1'-carbonylbis-1H-imidazole (0.006 mol) was added to a stirring mixture of intermediate 20 (0.0055 mol) in tetrahydrofuran (100 ml). The mixture was stirred at room temperature for 3 hours. N-methyl-2-propanamine (0.0073 mol) and triethylamine (0.01 mol) were added. The mixture was stirred at room temperature overnight. $H_2O$ was added. The precipitate was filtered off and dried. The residue was purified by column chromatography over silica gel (eluent: $CH_2Cl_2CH_3OH$ 98/2). The pure fractions were collected and the solvent was evaporated. The residue was boiled in ethanol. The mixture was cooled. The precipitate was filtered off and dried, yielding 1.8 g (50%) of (B-cis)-N-[4-[4-[4-[[4-(2,4-difluorophenyl)-4-(1H-1,2,4-triazol-1-yl-methyl)-1,3-dioxolan-2-yl]methoxy]phenyl]-1-piperazinyl]phenyl]-N'-methyl-N'-(1-methylethyl)urea (Comp. 54; mp. 186° C.; $\alpha_{20}^D = +18.27°$ (c=24.08 mg/5 ml in DMF)).

b) (B-cis)-N-[4-[4-[4-[[4-(2,4-difluorophenyl)-4-(1H-1,2,4-triazol-1-ylmethyl)-1,3-dioxolan-2-yl]methoxy]phenyl]-1-piperazinyl]phenyl]-N,N'-dimethyl-N'-(1-methylethyl) urea (comp. 56) was prepared analogous to compound 54 but trichloromethylchloroformate in $CH_2Cl_2$ was used instead of 1,1'-carbonylbis-1H-imidazole in tetrahydrofuran.

The compounds listed in table 1 were prepared in a similar manner as one of the above mentioned examples.

TABLE 1

| Comp No. | Ex. No. | X | $R^{1a}$ | $R^{1b}$ | -$R^3$-$R^4$- | $R^2$ | Physical data m.p. in °C. |
|---|---|---|---|---|---|---|---|
| 1 | B3a | N | H | F | C(=O)C(CH$_3$)$_2$ | CH$_2$CH$_3$ | 153.1; (±)-cis |
| 2 | B3a | CH | H | Cl | C(=O)C(CH$_3$)$_2$ | CH$_2$CH$_3$ | 200.3; (±)-cis |
| 3 | B3a | CH | H | F | C(=O)C(CH$_3$)$_2$ | CH$_2$CH$_3$ | 216.7; (±)-cis |
| 4 | B3a | CH | H | Cl | CH$_2$CH$_2$ | (CH$_2$)$_2$CH$_3$ | 203.8; (±)-cis |
| 5 | B3a | CH | H | Cl | CH$_2$C(CH$_3$)$_2$ | (CH$_2$)$_2$CH$_3$ | 182.4; (±)-cis |
| 6 | B3a | N | H | F | CH$_2$CH$_2$ | (CH$_2$)$_2$CH$_3$ | 174.2; (±)-cis |
| 7 | B3a | N | H | Cl | C(=O)C(CH$_3$)$_2$ | CH$_2$CH$_3$ | 169.2; (±)-cis |
| 8 | B3a | CH | H | Cl | CH$_2$CH$_2$ | CH(CH$_3$)C$_2$H$_5$ | 170.0; (±)-cis |
| 9 | B3a | N | H | Cl | CH$_2$C(CH$_3$)$_2$ | (CH$_2$)$_2$CH$_3$ | 142.9; (±)-cis |
| 10 | B3a | N | H | Cl | CH$_2$CH$_2$ | CH(CH$_3$)C$_2$H$_5$ | 159.5; (±)-cis |
| 11 | B3a | CH | H | F | CH$_2$CH$_2$ | CH(CH$_3$)C$_2$H$_5$ | 182.1; (±)-cis |
| 12 | B3a | CH | H | F | CH$_2$C(CH$_3$)$_2$ | (CH$_2$)$_2$CH$_3$ | 192.1; (±)-cis |
| 13 | B3a | N | H | F | CH$_2$C(CH$_3$)$_2$ | (CH$_2$)$_2$CH$_3$ | 146.1; (±)-cis |
| 14 | B3a | N | H | F | CH$_2$CH$_2$ | CH(CH$_3$)C$_2$H$_5$ | 174.0; (±)-cis |
| 15 | B4 | N | F | F | CH$_2$C(CH$_3$)$_2$ | CH$_2$CH$_3$ | 184.7; (±)-cis |
| 16 | B4 | N | F | F | CH$_2$C(CH$_3$)$_2$ | (CH$_2$)$_2$CH$_3$ | 174.0; (±)-cis |
| 17 | B4 | N | F | F | CH$_2$CH$_2$ | (CH$_2$)$_2$CH$_3$ | 184.7; (±)-cis |
| 18 | B4 | N | F | F | C(=O)CH(CH$_3$) | (CH$_2$)$_3$CH$_3$ | 162.2; (±)-cis |
| 19 | B4 | N | F | F | C(CH$_3$)$_2$C(=O) | CH$_2$CH$_3$ | 160.7; (±)-cis |
| 20 | B4 | N | F | F | C(=O)CH(CH$_2$CH$_3$) | CH$_2$CH$_3$ | 156.2; (±)-cis |
| 21 | B4 | N | F | F | CH$_2$CH$_2$ | CH(CH$_3$)C$_2$H$_5$ | 155.1; (±)-cis |
| 22 | B4 | N | Cl | Cl | CH$_2$CH$_2$ | (CH$_2$)$_2$CH$_3$ | 174.8; (±)-cis |
| 23 | B3a | CH | H | F | CH$_2$CH$_2$ | CH(CH$_3$)$_2$ | 203.6; (±)-cis |
| 24 | B3a | CH | H | F | CH$_2$CH$_2$ | CH$_2$CH$_3$ | 222.1; (±)-cis |
| 25 | B3a | CH | H | F | CH$_2$CH$_2$ | (CH$_2$)$_2$CH$_3$ | 209.7; (±)-cis |
| 26 | B3a | CH | H | F | CH$_2$CH$_2$ | (CH$_2$)$_3$CH$_3$ | 185.9; (±)-cis |
| 27 | B3a | CH | H | Cl | CH$_2$CH$_2$ | CH$_2$CH$_3$ | 239.8; (±)-cis |
| 28 | B3a | CH | H | Cl | CH$_2$CH$_2$ | CH(CH$_3$)$_2$ | 203.3; (±)-cis |
| 29 | B3a | CH | H | Cl | CH$_2$CH$_2$ | (CH$_2$)$_3$CH$_3$ | 209.9; (±)-cis |
| 30 | B3a | CH | F | F | CH$_2$CH$_2$ | (CH$_2$)$_2$CH$_3$ | 168.8; (±)-cis |
| 31 | B3a | CH | H | F | CH$_2$CH$_2$ | CH(CH$_3$)C$_2$H$_5$ | 200.8; (±)-trans |
| 32 | B3a | CH | F | F | CH$_2$CH$_2$ | CH$_2$CH$_3$ | 205.7; (±)-cis |
| 33 | B3a | CH | F | F | CH$_2$CH$_2$ | (CH$_2$)$_3$CH$_3$ | 180.8; (±)-cis |
| 34 | B3a | CH | F | F | CH$_2$CH$_2$ | CH(CH$_3$)$_2$ | 163.1; (±)-cis |
| 35 | B3a | CH | F | F | CH$_2$CH$_2$ | CH(CH$_3$)C$_2$H$_5$ | 137.3; (±)-cis |
| 36 | B3a | CH | H | F | CH$_2$CH$_2$ | CH$_2$CH(CH$_3$)$_2$ | 169.6; (±)-cis |
| 37 | B3a | CH | H | Cl | CH$_2$CH$_2$ | CH$_2$CH(CH$_3$)$_2$ | 184.8; (±)-cis |
| 38 | B3a | N | H | Cl | CH$_2$CH$_2$ | CH$_2$CH$_3$ | 194.0; (±)-cis |
| 39 | B3a | CH | H | F | CH$_2$CH$_2$ | cyclopentyl | 220.1; (±)-cis |
| 40 | B3a | N | H | F | CH$_2$CH$_2$ | CH(CH$_3$)$_2$ | 186.4; (±)-cis |
| 41 | B3a | N | F | F | CH$_2$CH$_2$ | CH(CH$_3$)$_2$ | 168.5; (±)-cis |
| 42 | B3a | CH | H | F | CH$_2$CH$_2$ | CH$_3$ | 241.5; (±)-cis |
| 43 | B3a | N | H | F | CH$_2$CH$_2$ | (CH$_2$)$_3$CH$_3$ | 169.0; (±)-cis |
| 44 | B3a | CH | H | F | CH$_2$CH$_2$ | CH(C$_2$H$_5$)$_2$ | 152.9; (±)-cis |
| 45 | B3a | CH | H | F | CH$_2$CH$_2$ | CH(CH$_3$)C$_2$H$_5$ | 162.6; (±)-cis |
| 46 | B1 | N | F | F | C(=O)N[(CH$_2$)$_2$CH$_3$]C(=O) | CH$_2$CH$_3$ | 156.9; 2R-cis |
| 47 | B2 | N | F | F | C(=O)N[(CH$_2$)$_2$CH$_3$]C(=O) | CH$_2$CH$_3$ | 158.8; 2S-cis |
| 48 | B1 | N | F | F | C(=O)C(CH$_3$)$_2$C(=O) | CH$_2$CH$_3$ | 126.1; 2R-cis |
| 49 | B2 | N | F | F | C(=O)C(CH$_3$)$_2$C(=O) | CH$_2$CH$_3$ | 114.8; 2S-cis |
| 50 | B1 | N | F | F | CH$_2$CH$_2$ | CH(CH$_3$)$_2$ | 177.3; 2R-cis |
| 51 | B3a | N | F | F | CH$_2$CH$_2$ | CH(CH$_3$)$_2$ | 177.8; 2S-cis |
| 52 | B3b | N | F | F | CH$_2$CH$_2$ | CH(CH$_3$)$_2$ | 2S-cis; HCl(1:1) |

TABLE 2

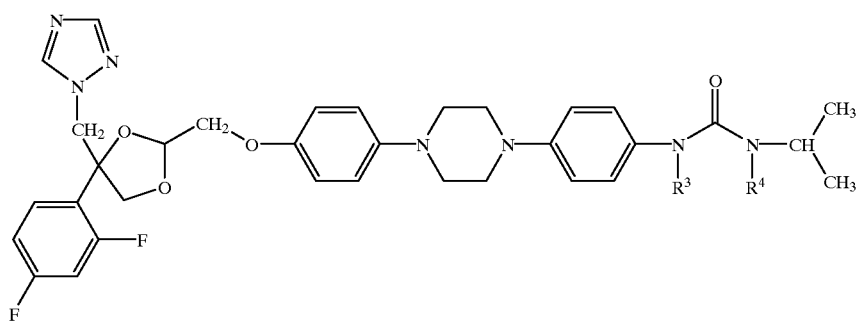

| Comp No. | Ex No. | $R^3$ | $R^4$ | Physical data |
|---|---|---|---|---|
| 53 | B5 | H | H | (2S-cis); mp. 196° C.; $\alpha_{20}^D$ = +18.64° (c = 24.68 mg/5 ml in DMF) |
| 54 | B6a | H | $CH_3$ | (2S-cis); HCl (1:1); mp. 186° C.; $\alpha_{20}^D$ = +18.27° (c = 24.08 mg/5 ml in DMP) |
| 55 | B5 | $CH_3$ | H | (2S-cis); mp. 112° C.; $\alpha_{20}^D$ = +17.57° (c = 24.76 mg/5 ml in DMF) |
| 56 | B6b | $CH_3$ | $CH_3$ | (2S-cis); $\alpha_{20}^D$ = +17.42° (c = 24.68 mg/5 ml in DMF) |

C. Pharmacological Examples

Example C.1: Measurement of Antifungal Activity in Vitro

Test compounds were dissolved at a concentration of $10^{-2}$ M in dimethyl sulfoxide (DMSO) and diluted into CYG broth (Odds, F. C. *Antimicrobial Agents and Chemotherapy* 1992; 36: 1727–1737) to give a final concentration of 25 µM and, in most tests, 5 µM. For some compounds the tests were done at 100, 10, 1.0 and 0.1 µM. Cultures were inoculated with *Candida.kefyr* to an initial concentration of $10^4$/ml and with *Trichophyton rubrum* to an equivalent concentration determined by turbidimetry. Cultures were incubated in the wells of microdilution plates at 37° C. for 48 h (*C. kefyr*) and at 30° C. for 5–7 days (*T. rubrum*). Growth in wells containing test compounds was estimated turbidimetrically as a percentage of growth in compound-free controls and the lowest concentration of compound that inhibited the growth of an isolate below 35% of control growth was recorded as the lowest active dose (LAD).

TABLE 2

| Comp. No. | LAD (µM) vs. | |
|---|---|---|
| | C. keyr | T. rubrum |
| 1 | ≦25 | >25 |
| 2 | ≦5 | ≦5 |
| 3 | ≦25 | ≦5 |
| 4 | ≦5 | ≦5 |
| 5 | ≦25 | ≦5 |
| 9 | ≦25 | ≦25 |
| 12 | ≦25 | ≦5 |
| 13 | ≦5 | ≦5 |
| 19 | ≦5 | ≦25 |
| 20 | ≦5 | >25 |
| 21 | ≦0.1 | ≦0.1 |
| 23 | ≦5 | ≦5 |
| 24 | ≦25 | ≦5 |
| 25 | ≦5 | ≦5 |
| 26 | ≦25 | ≦5 |
| 27 | ≦5 | ≦5 |
| 28 | ≦25 | ≦5 |
| 29 | ≦25 | ≦5 |
| 30 | ≦5 | ≦5 |

TABLE 2-continued

| Comp. No. | LAD (µM) vs. | |
|---|---|---|
| | C. keyr | T. rubrum |
| 32 | ≦25 | ≦5 |
| 34 | ≦5 | ≦5 |
| 35 | ≦25 | ≦5 |
| 40 | ≦25 | ≦5 |
| 41 | ≦0.1 | ≦0.1 |
| 42 | ≦5 | ≦5 |
| 44 | ≦5 | ≦5 |
| 46 | 1 | 100 |
| 47 | >100 | 1 |
| 48 | 10 | >100 |
| 49 | 1 | 1 |
| 50 | 1 | 1 |
| 51 | ≦0.1 | ≦0.1 |
| 52 | ≦0.1 | ≦0.1 |

D. Composition Examples

"Active ingredient" (A.I.) as used throughout these examples relates to a compound of formula (I), a pharmaceutically acceptable addition salt or a stereochemically isomeric form thereof.

Example D.1: Nanoparticulate Suspension

A solution of water for injections and Pluronic™ F108 (540 g) is prepared. The grinding medium, ZrO stabilised with magnesia, and the A.I. in a particulate form (540 g) are added. The resulting suspension is dispersed at room temperature using a rolling mill for 14 days. The grinding medium is separated from the suspension which is then diluted with water for injections to a total volume of 54 liters. All manipulations are performed aseptically according to FDA and European guidelines.

Example D.2: Meltextruded Tablet

A 40/60 (w/w) mixture of A.I. (21.74 kg) and hydroxypropyl methylcellulose 2910 5 mPa.s[(1)] or HPMC 2910 5 mPa.s (32.11 kg) are both sieved and mixed in a planetary mixer until the mixture is homogenous. 1500 g of this mixture is fed into a twin screw melt extruder of the type APV-Baker MP19 L/D 15 having the following operating parameters: temperature of the first compartment is 245° C., temperature of the second compartment is 265° C., the twin screw has a rate of 20–300 revolutions/min and is extruded during 120 minutes. The extrudate is brought in a hammer mill of type Fitzmill, the mesh of the sieve is 0.125 inch and revolving speed is 1640 revolutions per minute. The milled extrudate is again brought in a hammer mill, this time with a sieve of mesh 0.063 inch and a revolving speed of 1640 revolutions per minute. Subsequently, microcrystalline cellulose (351 g, 21% (w/w)), Crospovidone (117 g, 7% (w/w)), Aerosil (colloidal silicon dioxide) (5 g, 0.3% (w/w)) and Sterotex (8 g, 0.5% (w/w)) are sieved and mixed together with the milled extrudate (1169 g, 71% (w/w)) using a planetary mixer until a homogenous mixture is obtained. This mixture is used to obtain oval biconvex half-scored tablets.

Example D.3: Oral Solution 100 ml of propylene glycol is treated with 3.76 ml concentrated HCl, stirred and slightly heated. 10 g A.I. is added and stirring is continued until homogeneous. In a separate vessel, 400 g hydroxypropyl-β-cyclodextrin is dissolved in 400 ml distilled water. The solution of the A.I. is added slowly to the cyclodextrin solution while stirring. A sorbitol (70%) non-crystallizing solution (190 ml) is added and stirred till homogeneous. Sodium saccharin (0.6 g) is dissolved in 50 ml distilled water and added to the mixture. The pH of the mixture is adjusted with a 10 N NaOH solution to pH 2.0±0.1. The resulting solution is diluted with distilled water to an end volume of 1 litre. A pharmaceutical dosage form is obtained by filtering the previous solution and filling it into suitable containers, e.g. in 100 ml glass bottles with a screw cap.

Example D.4: 2% Topical Gel

To a solution of hydroxypropyl β-cyclodextrin (200 mg) in purified water is added the A.I. (20 mg) while stirring. Hydrochloric acid is added until complete solution and the sodium hydroxide is added until pH=6.0. This solution is added to a dispersion carrageenan PJ (10 mg) in propylene glycol (50 mg) while mixing. While mixing slowly the mixture is heated to 50° C. and allowed to cool to about 35° C. whereupon ethyl alcohol (95%; 50 mg) is added. Purified water is added q.s. ad 1 g and the mixture is mixed until homogeneous.

Example D.5: 2% Cream

Stearyl alcohol (75 mg), cetyl alcohol (20 mg), sorbitan monostearate (20 mg) and isopropyl myristate (10 mg) are introduced in a doublewall jacketed vessel and heated until the mixture has completely molten. This mixture is added to a seperately prepared mixture of purified water, propylene glycol (200 mg) and polysorbate 60 (15 mg) having a temperature of 70 to 75° C. while using a homogenizer for liquids. The resulting mixture is allowed to cool to below 25° C. whle continouosly mixing. A solution of A.I. (20 mg), polysorbate 80 (1 mg) and purified water q.s. ad 1 g and a solution of sodium sulfite anhydrous (2 mg) in purified water are next added to the emulsion while continouosly mixing. The cream is homogenized and filled into suitable tubes.

Example D.6: 2% Cream

A mixture of A.I. microfine (2 g), phosphatidyl choline (20 g), cholesterol (5 g) and ethyl alcohol (10 g) is stirred and heated at 55–60° C. until complete solution and is added to a solution of methyl paraben (0.2 g), propyl paraben (0.02 g), disodium edetate (0.15 g) and sodium chloride (0.3 g) in purified water (ad 100 g) while homogenizing. Hydroxypropylmethylcellulose (1.5 g) in purified water is added and the mixing is continued until swelling is complete.

Example D.7: Beads Formulation

An inox vessel is charged with methylene chloride (375 kg) and denatured ethanol (250 kg) through a filter (5μ). A.I. (21.74 kg) and hydroxypropyl methylcellulose 2910 5 mPa.s (32.61 kg) is added while stirring. Stirring is continued until complete dissolution is obtained.

A separate inox vessel is charged with methylene chloride (21.13 kg) and polyethylene glycol 20000 (3.913 kg) while stirring. Denatured ethanol (14.09 kg) is added and the spraying solution is stirred until homogeneous.

A fluidized-bed granulator equipped with a 18 inch Wurster (bottom spray) insert is loaded with 25–30 mesh (600–700 μm) sugar spheres (41.74 kg). The spheres are warmed with dry air of 50°–55° C. The fluidizing air volume is controlled by opening the exhaust air valve to approximately 50% of its maximum in the beginning, increasing up to 60% at the end of the spraying process. The previously prepared spraying solution is then sprayed on the spheres moving in the apparatus at an initial delivery rate of about 600 to 700 g.min$^{-1}$ at an atomizing air pressure of about 3.5 kg/cm$^2$ (0.343 MPa). After delivery of about 30% of the spraying solution, the delivery rate is increased to 700–800 g/min. When the spraying process is completed, the coated spheres are dried by further supplying dry air of 50°–55° C. for about 10 minutes. The coated spheres are then allowed to cool in the apparatus by supplying dry air of 20–25° C. for about 10 to 20 minutes.

d) In-between Drying

The coated spheres are introduced in a vacuum tumbler-drier and dried for at least 24 hours, preferably about 36 hours, at a temperature of about 80° C. at a pressure of about 200–300 mbar (20–30 kPa). The tumbler-drier was operated at its minimal rotation speed (2 to 3 rpm). The dried coated spheres were sieved with a sieve (Sweco S24C; sieve mesh width 1.14 mm).

e) Seal-coating Process

The dried coated spheres were introduced again in the fluidized-bed granulator equipped with the Wurster insert and warmed with dry air of 50–55° C. The previously prepared seal-coating spraying solution was then sprayed on the coated spheres moving in the apparatus. The solution was sprayed at an delivery rate of about 400 to 500 g.min$^{-1}$, at an atomizing air pressure of about 2.5 bar (0.25 MPa). When the spraying process was completed, the beads were dried by further supplying dry air of 50–55° C. for 10 min. The coated spheres were then allowed to cool in the apparatus by supplying dry air of 20°–25° C. for about 5 to 15 minutes. The beads were removed from the apparatus and stored in suitable containers.

What is claimed is:

1. A compound having the formula

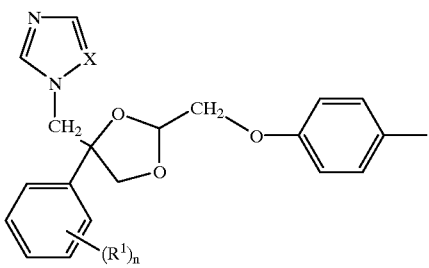

(I)

a N-oxide form, a pharmaceutically acceptable acid addition salt or a stereochemically isomeric form thereof, wherein n is 2;

X is N or CH;

$R^1$ is fluoro;

$R^2$ is hydrogen; $C_{3-7}$alkenyl; $C_{3-7}$alkynyl; aryl; $C_{3-7}$cycloalkyl; $C_{1-6}$alkyl or $C_{1-6}$alkyl substituted with hydroxy, $C_{1-4}$alkyloxy, $C_{3-7}$cycloalkyl; or aryl;

$R^3$ and $R^4$ each independently are hydrogen, $C_{1-6}$alkyl, $C_{3-7}$cycloalkyl or aryl; or $R^3$ and $R^4$ taken together form a bivalent radical —$R^3$—$R^4$— of formula:

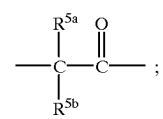  (a)

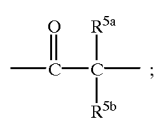  (b)

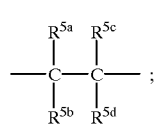  (c)

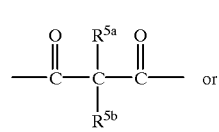  (d)

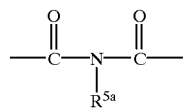  (e)

wherein $R^{5a}$, $R^{5b}$, $R^{5c}$, $R^{5d}$ each independently are hydrogen, $C_{1-6}$alkyl or aryl; and aryl is phenyl or phenyl substituted with one, two or three substituents selected from halo, nitro, cyano, amino, hydroxy, $C_{1-4}$alkyl, $C_{1-4}$alkyloxy or trifluoromethyl.

2. A compound as claimed in claim 1 wherein $R^3$ and $R^4$ are independently hydrogen or $C_{1-6}$alkyl, or $R^3$ and $R^4$ form a bivalent radical —$R^3$—$R^4$— of formula (a), (b), (c), (d) or (e).

3. A compound as claimed in claim 2 wherein $R^2$ is $C_{3-7}$cycloalkyl or $C_{1-6}$alkyl.

4. A compound as claimed in claim 3 wherein the substituents on the 1,3-dioxolane ring have a cis configuration.

5. A compound as claimed in claim 4 wherein the phenyl ring attached in the 4-position of the 1,3-dioxolane ring is a 2,4-difluorophenyl ring; $R^3$ and $R^4$ form a bivalent radical —$R^3$—$R^4$— of formula (c) wherein $R^{5a}$, $R^{5b}$, $R^{5c}$ and $R^{5d}$ are hydrogen; and $R^2$ is methyl, ethyl, propyl, butyl, 1-methylethyl or 1-methylpropyl.

6. A pharmaceutical composition comprising a pharmaceutically acceptable carrier, and as active ingredient a therapeutically effective amount of a compound as claimed in claim 1.

7. A process of preparing a compound as claimed in claim 1, comprising a) O-alkylating an appropriately substituted phenol of formula (III) with an alkylating reagent of formula (II)

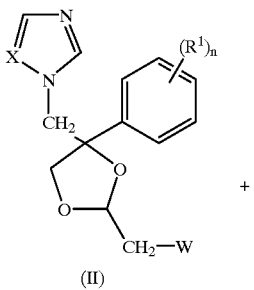

(II)

+

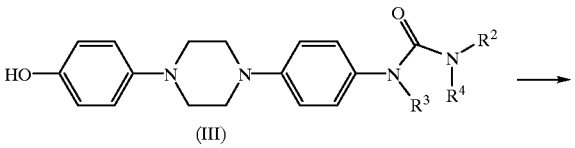

(III)

→

(I)

wherein W represents an appropriate reactive leaving group, and n, X, $R^1$ to $R^4$ are as defined in claim 1, in a suitable reaction-inert solvent in the presence of an appropriate base and optionally under an inert atmosphere;

b) transacetalating an acetal of formula (V) with a 1,2-diol of formula (IV) by stirring the reactants in an appropriate reaction-inert solvent in the presence of a suitable acid catalyst,

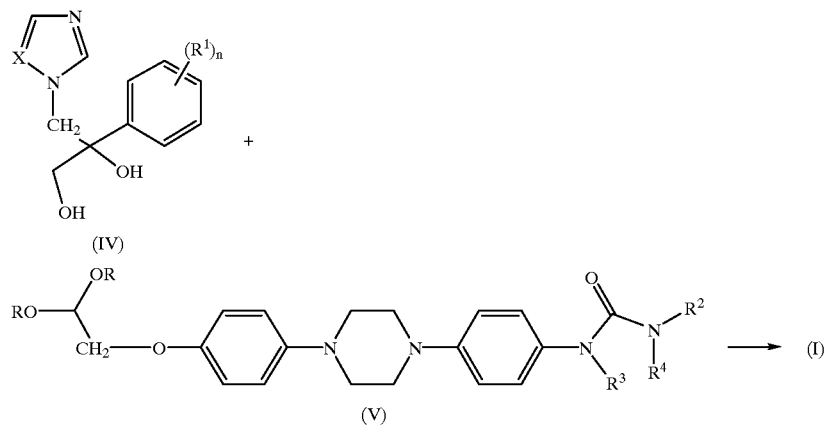

wherein R represents an alkyl group or both R radicals taken together may also form a bivalent alkanediyl radical, and n, X, $R^1$ to $R^4$ are as defined in claim 1;

c) by cyclizing an intermediate of formula (VI) or (IX) with respectively an amine of formula (VII) or (VIII) optionally in a reaction-inert solvent and optionally in the presence of a base;

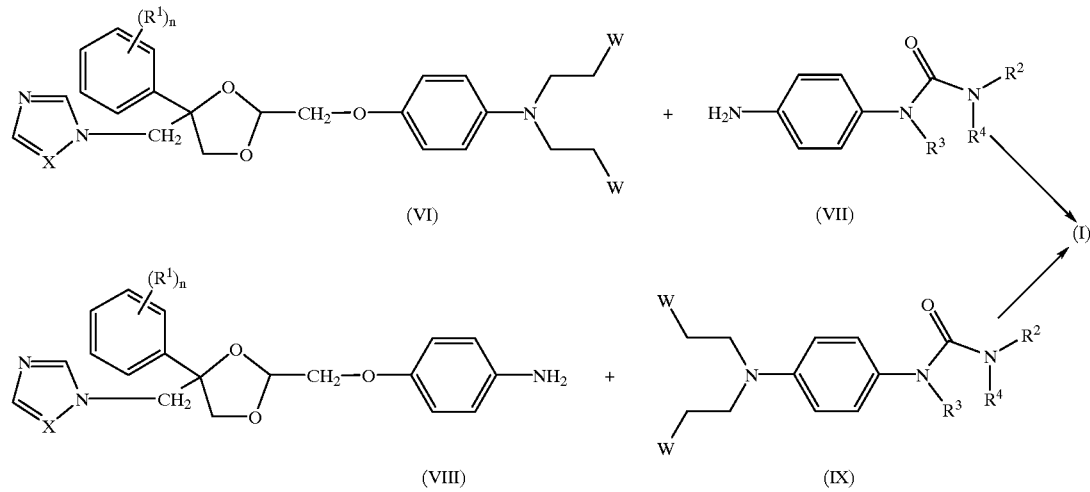

wherein W represents an appropriate reactive leaving group, and n, X, $R^1$ to $R^4$ are as defined in claim 1;

d) N-alkylating a compound of formula (X) with an alkylating reagent of formula $R^2$—W (XI)

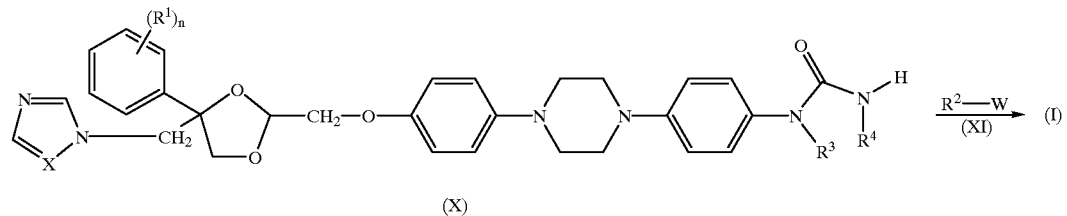

wherein W represents an appropriate reactive leaving group, and n, X, $R^1$ to $R^4$ are as defined in claim 1;

e) reacting an intermediate of formula (XVII) with an isocyanate $R^2$—N=C=O in a reaction-inert solvent, thus obtaining a compound of formula (I-a);

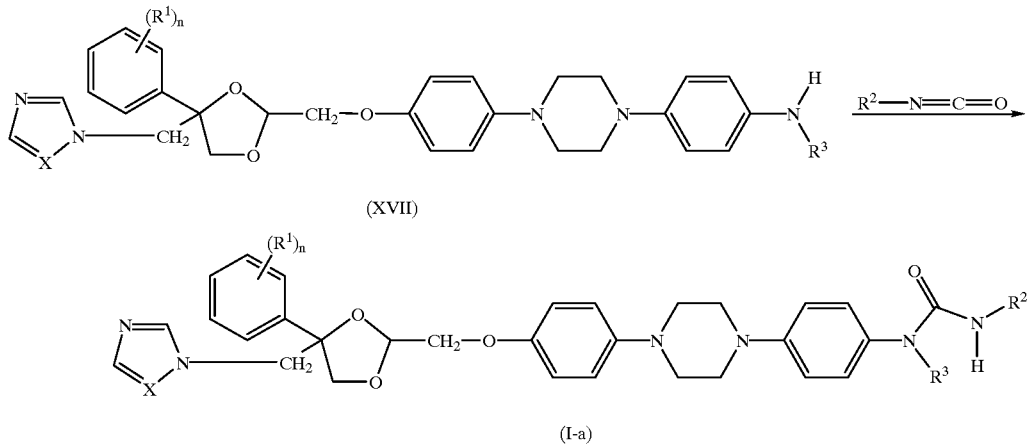

wherein n, X, $R^1$ to $R^3$ are as defined in claim 1; thus obtaining a compound of formula (I-a);

f) reacting an intermediate of formula (XVIII) with an intermediate $NHR^2R^{4'}$ wherein L is a suitable leaving group, n, X, $R^1$ to $R^3$ are as defined in claim 1, $R^{4'}$ is defined as hydrogen, $C_{1-6}$alkyl, $C_{3-7}$cycloalkyl and aryl, in a reaction-inert solvent and in the presence of an appropriate base; and wherein reactive amino groups in $R^2$, in case they are present, are protected with a protective group P, and subsequently, if necessary, deprotected using art-known deprotection techniques; thus obtaining a conpound of formula (I-b);

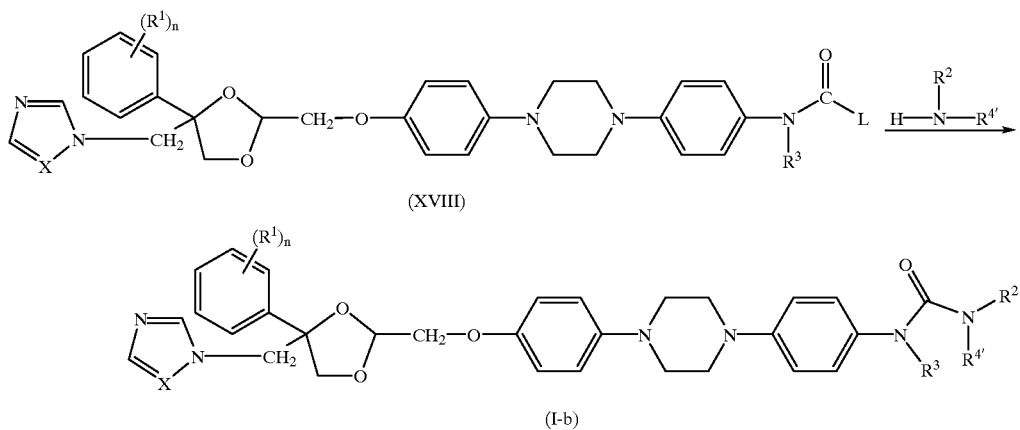

and, if desired, converting compounds of formula (I) into each other following art-known transformations; and further, if desired, converting the compounds of formula (I), into a therapeutically active non-toxic acid addition salt by treatment with an acid, or conversely, converting the acid addition salt form into the free base by treatment with alkali; and, if desired, preparing stereochemically isomeric forms or N-oxide forms thereof.

8. The combination of a compound of formula (I) as defined in claim 1 and another antifungal compound.

9. A product containing (a) a compound of formula (I) as defined in claim 1, and (b) another antifungal compound, as a combined preparation for simultaneous, separate or sequential use in antifungal treatment.

10. A pharmaceutical composition comprising a pharmaceutically acceptable carrier and as active ingredients (a) a compound of formula (I) as defined in claim 1, and (b) another antifungal compound.

11. A method of treating fungal infections in a warm-blooded animal in need thereof comprising administering to the warm-blooded animal an effective amount of a compound of claim 1.

12. A method of treating fungal infections in a warm-blooded animal in need thereof comprising administering to the warm-blooded animal an effective amount of the combination of claim 8.

13. A pharmaceutical composition made by mixing a compound of claim 1 with a pharmaceutically acceptable carrier.

14. A process of preparing a pharmaceutical composition comprising mixing a compound of claim 1 with a pharmaceutically acceptable carrier.

* * * * *

UNITED STATES PATENT AND TRADEMARK OFFICE
CERTIFICATE OF CORRECTION

PATENT NO. : 6,387,906 B1 Page 1 of 1
DATED : May 14, 2002
INVENTOR(S) : Lieven Meerpoel et al.

It is certified that error appears in the above-identified patent and that said Letters Patent is hereby corrected as shown below:

Title page,
Item [56], References Cited, add:
-- OTHER REFERENCES
Rodriguez & Hitchcock, Exp. Opin. Ther. Patents (1997), Vol. 7, No. 8, 829-841 --

Signed and Sealed this

Second Day of December, 2003

JAMES E. ROGAN
*Director of the United States Patent and Trademark Office*